United States Patent [19]

Busse

[11] 4,391,735

[45] Jul. 5, 1983

[54] CLEANING AND REGENERATING ETHYLENE OXIDE CATALYSTS

[75] Inventor: Paul J. Busse, Omaha, Nebr.

[73] Assignee: InterNorth, Inc., Omaha, Nebr.

[21] Appl. No.: 284,207

[22] Filed: Jul. 17, 1981

[51] Int. Cl.$^3$ .................. B01J 23/96; B01J 23/50; C07D 301/10

[52] U.S. Cl. ............................. 252/413; 252/143; 252/153; 252/170; 252/414; 549/534

[58] Field of Search ............... 252/413, 414, 143, 153, 252/170

[56] References Cited

U.S. PATENT DOCUMENTS

| | | | |
|---|---|---|---|
| 3,914,132 | 10/1975 | Sutton | 252/153 |
| 3,965,036 | 6/1976 | Himmelstein | 252/414 |
| 4,033,903 | 7/1977 | Makwell | 252/476 |
| 4,155,875 | 5/1979 | Yamaguchi et al. | 252/414 |
| 4,156,030 | 5/1979 | Eggen | 426/430 |
| 4,186,106 | 1/1980 | Rebsdat et al. | 252/414 |
| 4,941,764 | 3/1983 | Hensarling et al. | 260/412.3 |

*Primary Examiner*—P. E. Konopka
*Attorney, Agent, or Firm*—Donald F. Haas

[57] ABSTRACT

A composition and method for removing alkali metal-containing impurities from supported silver catalysts wherein the composition is comprised of an inert organic liquid and a solubilizing agent. The method is used prior to regeneration of the catalyst with cesium, rubidium, or mixtures thereof to improve the selectivity of the regenerated catalyst.

15 Claims, No Drawings

CLEANING AND REGENERATING ETHYLENE OXIDE CATALYSTS

BACKGROUND OF THE INVENTION

This invention relates to a composition and the use there of for cleaning used supported silver catalysts as part of a process for regenerating such catalysts. Specifically, the invention relates to the removal of alkali metal-containing impurities from the used catalyst.

Supported sliver-based catalysts have been used industrially for many years for the oxidation of ethylene to ethylene oxide with oxygen or air. Most of the ethylene which is reacted is converted into ethylene oxide on the silver-impregnated catalyst support material and the remainder of the ethylene is converted almost exclusively to carbon dioxide and water. The goal is to react as much ethylene as possible, i.e. high productivity, such that the greater amount of the ethylene is converted to ethylene oxide, i.e. high selectivity.

It is known that the selectivity of these silver catalysts tends to decrease after the catalysts have been used for a number of years. I have found that one reason for the decrease in selectivity is the build-up of alkali metal-containing impurities on the catalysts. The decrease in selectivity results in less favorable economy of operation. It becomes advantageous to reactivate or regenerate the catalysts since an increase in selectivity of as little as one percentage point (selectivity equals 100 times the amount of ethylene converted to ethylene oxide divided by the total amount of ethylene consumed) can and will result in the savings of many thousands of dollars in a commercial operation.

There are several known methods for reactivating or regenerating silver catalysts. U.S. Pat. Nos. 4,051,068 issued Sept. 27, 1977, 4,123,385 issued Oct. 31, 1978, 4,125,480 issued Nov. 14, 1978, and 4,177,169 issued Dec. 4, 1979 disclose four such methods for regenerating silver catalysts. An essential part of the process of U.S. Pat. No. 4,125,480 is a washing step wherein the used catalyst is washed with one to ten times its volume of water or a mixture of water and an organic solvent before additional promoters are deposited on the catalyst. Treatment with water or water-containing solutions can be detrimental to catalyst performance. In addition, exposure of the reactors to aqueous solutions can result in corrosion of the reactor and the formation of iron oxides which can be detrimental to the ethylene oxide manufacturing process.

U.S. Pat. No. 4,186,106 issued Jan. 29, 1980 discloses a process to improve the activity of supported silver catalysts which comprises washing the catalyst with an inert organic liquid and then applying cesium, rubidium, or a mixture thereof to the catalyst. The use of such non-aqueous solvents may provide adequate cleaning of the catalyst and eliminate the problems involved with exposure of the catalyst and/or reactor to an aqueous environment. There is no mention of the deleterious effects of alkali metal-containing impurities on the catalyst. Furthermore, I have found that less washings (and/or washing time) are required to remove the same amount of alkali metal-containing impurities if a solubilizing agent is included in the inert organic liquid prior to the washing of the catalyst than if no solubilizing agent is used. Many inert organic liquids are ineffective in removing alkali metal contaminants by themselves, but become very effective with the inclusion of a solubilizing agent.

SUMMARY OF THE INVENTION

The present invention relates to a composition for removing alkali metal-containing impurities from supported silver catalysts which have been used for the direct oxidation of ethylene to ethylene oxide. The composition comprises an inert organic liquid and about 0.1% to about 10%, preferably about 0.1% to about 5%, of a solubilizing agent. The preferred inert organic liquid is methanol and the preferred solubilizing agent is salicylic acid.

The above composition is used to remove alkali metal-containing impurities from the silver supported catalysts merely by washing the catalysts with the above composition. The washing step is preferably carried out from 1 to 25 times, depending upon the amount of alkali metal-contamination, to insure adequate removal of the alkali metal-containing impurities. This washing process can be included as an integral part of a process for regenerating used ethylene oxide catalysts. In such a process, the catalyst is first washed as described above and then from 1 to 1000 parts, per one million parts of catalyst, of cesium, rubidium, or a mixture thereof, is applied to the catalyst.

DETAILED DESCRIPTION OF THE INVENTION

There are many inert organic liquids which can be used in the process of the present invention. There are two main qualifications. First, they must remove the alkali metal-containing impurities and second, they must not poison or damage the catalyst to a noticeable degree such that its productivity and/or selectivity are reduced. Inert organic liquids which are useful in the present invention include aliphatic, alicyclic, or aromatic hydrocarbon, ethers, alcohols, and ketones. Aliphatic or aromatic esters amines, amides, and aldehydes can also be used, as well as nitriles. If the catalyst is to be regenerated as described below, amines should not be used because the selectivity is adversely affected. Amines can be used if only the washing step is to be used. The reason for this is unknown. The preferred organic liquid for use in this invention is methanol, but acetone, tetrahydrofuran, and acetonitrile can also be used with highly advantageous results.

As stated above, it is critical to the performance of the present invention that a solubilizing agent be included in the inert organic liquid prior to its being used to wash the used silver catalyst. Generally, it is preferred to use at least about 0.1% by weight and no more than about 10% by weight, preferably about 0.1% to about 5% of the solubilizing agent. Generally, if less than about 0.1% is used, the number of washings (and/or washing time) increases and more wash solution is required. Also, there is very little advantage obtained by using the solubilizing agent at such low concentrations. Generally, more than 10% is not necessary because very little additional advantage is obtained by using more and the problem of depositing solubilizing agent on the catalyst is alleviated. The 0.1% to 5% range is preferred because it provides a reasonably fast rate of dissolution of the alkali metal-containing contaminants while not leaving very much solubilizing agent deposited on the catalyst.

Suitable solubilizing agents for use in the present invention include aliphatic or aromatic acids and amines, and crown ethers. As above, amines should not be used if the catalyst is to be regenerated after the washing step. Acetic, propionic, lactic, and salicylic acids, and ethylenediamine are particularly preferred solubilizing agents for use in the present invention.

To wash the used catalyst, it is necessary to bring the catalyst into direct contact with the washing composition and then remove the major portion of the washing composition from the catalyst. One particularly preferred method for washing used silver catalysts is described in my co-pending application, entitled Process For The Removal Of Potassium From Used Ethylene Oxide Catalysts, Ser. No. 284,208, filed concurrently herewith. The washing procedures described in the aforementioned U.S. Pat. No. 3,186,106 can also be used. Another preferred method comprises dissolving the alkali metal-containing contaminants by soaking the used catalyst in the composition of the present invention for a period of about 0.1 hour to about 4 hours, draining away the liquid, and adding fresh liquid. It is important that the impurities first be dissolved and then diluted in subsequent treatments. Normally, four hours is sufficient to dissolve and dilute the impurities. This can be accomplished by using a longer washing time for the first treatment to obtain dissolution and then using shorter washing times for subsequent treatments to obtain dilution. Alternatively, the first treatment could be shorter and the subsequent treatments longer wherein both dissolution and dilution occur during each treatment.

This process is preferably carried out from 1 to 25 times to insure that all or most of the alkali metal-containing impurities are removed from the catalyst. The number of washings required is dependent upon the degree of alkali metal contamination on the catalyst. Preferably, the catalyst is washed until the alkali metal concentration is lowered to 20 parts per million or less to achieve better catalyst performance. When the solubilizing agent is used, less washings (and/or washing time) are required to achieve this goal than if the inert organic liquid alone is used.

The catalyst is then dried by any convenient method such as by evaporation of the liquid at elevated temperature, preferably at or below the boiling point of the inert organic liquid. The catalyst is then ready to be used again to manufacture ethylene oxide. The catalyst can be regenerated according to the processes disclosed in U.S. Pat. Nos. 4,051,068, 4,123,385, 4,125,480, and 4,177,169 discussed above. It is preferred that from 1 to 1000 parts per million of cesium, rubidium, or mixtures thereof be deposited upon the catalyst.

The following examples are meant only to illustrate the invention and not to limit it in any way.

EXAMPLE 1

A used sodium and barium promoted silver-containing ethylene oxide catalyst was washed three times with a solution of 5 weight percent acetic acid in methanol. The washing was conducted at room temperature and each portion of the wash solution was allowed to contact the catalyst for 30 minutes. The catalyst pellets were dried at 60° C. for one hour between washings and after the final washing. By this process, the sodium content of the catalyst was reduced from 0.28 percent to 0.04 percent. The barium and silver content of the catalyst was essentially unchanged.

EXAMPLES 2-7

The catalyst samples used in these examples were comprised of one-quarter inch spheres of supported silver-based catalysts which had been used for a long continuous period of time to manufacture ethylene oxide and were contaminated with potassium-containing impurities. The washing procedure in each case consisted of soaking 60 grams of the catalyst in 60 milliliters of the corresponding wash solvent and allowing the catalyst to stand for two hours. The catalysts were then drained of solvent and fresh solvent was added. The wash process was continued until the potassium level in the catalyst was determined to be at or below 20 parts per million of the dried catalyst weight. The catalysts were dried at 60° C. by evaporation and evaluated in a bench scale reactor operated in the range of 300°-500° F. with an inlet gas composition of 7 percent oxygen, 18 percent ethylene, 8 percent carbon dioxide, and one part per million of ethylene dichloride at a gas hourly space velocity (GHSV) of 240 $h^{-1}$.

The following table shows the number of washes which are necessary with each wash solvent to obtain the desired level of potassium. The term "selectivity at 1.5 percent ΔEO" means the selectivity at a productivity of 1.5 percent. In other words, 1.5 percent more ethylene oxide came out of the reactor than went in.

TABLE 1

| Example | Wash Solvent | Washes | Selectivity @ 1.5% EO | T °F. |
|---|---|---|---|---|
| 2 | None | 0 | a | 485 |
| 3 | 3% acetic acid/methanol | 10 | 69.2 | 490 |
| 4 | 3% salicylic acid/methanol | 7 | 68.8 | 491 |
| 5 | 3% lactic acid/methanol | 6 | b | 488 |
| 6 | 3% propionic acid/methanol | 9 | 67.1 | 498 |
| 7 | 3% ethylenediamine/methanol | 13 | 67.2 | 475 | a Could not achieve 1.5% ΔEO. The productivity was 0.77% ΔEO and the selectivity was 70%.
b 1.5% ΔEO could not be achieved. The productivity was 0.88% ΔEO and the selectivity was 70.4%.

The catalyst samples which were washed according to the present invention were far superior to the catalyst sample which was not so treated. Even though the selectivity of the untreated sample was higher, the productivity level which could be obtained was so much lower that it could not possibly have any commercial application. For accurate comparison, the selectivity must be compared at the same productivity. Normally, the minimum productivity for a commercial catalyst is 1.2 percent ΔEO at 490° F. If it was to have been of commercial quality the untreated catalyst should have had a selectivity of about 76 at such a low productivity. In Examples 3, 4, 6 and 7, the method of present invention produced a catalyst with an improved selectivity. It is thought that the results of Example 5 were unsatisfactory because of some unknown experimental error since this wash solvent performed well in Example 13 and other tests.

EXAMPLES 8-17

The following examples were carried out using the same catalyst used in Examples 2 through 7. The catalyst samples were washed the indicated number of times to reduce the potassium concentration to less than 20 parts per million. The same wash procedure as used for the above examples was used in this example. Subsequent to the washings, the catalyst samples were soaked in a cesium acetate in methanol solution for two hours. After that time, the catalyst samples were drained and dried at 60° C. and then used in a bench scale reactor to make ethylene oxide. The inlet gas composition was 7 percent oxygen, 18 percent ethylene, 8 percent carbon dioxide, and 1 part per million of ethylene dichloride at a GHSV of 240 $h^{-1}$. The reactor temperature ranged from 350° to 500° F. The results of these experiments are shown in the following table.

TABLE 2

| Example | Wash Solvent | Washes | Selectivity @ 1.5 ΔEO | T °F. |
|---|---|---|---|---|
| 8 | None | 0 | 69.3 | 453 |
| 9 | Methanol | 13 | 71.6 | 465 |
| 10 | 3% acetic acid/methanol | 9 | 71.3 | 457 |
| 11 | 3% acetic acid/acetone | 11 | 71.1 | 500 |
| 12 | 3% propionic acid/methanol | 8 | 71.7 | 458 |
| 13 | 3% lactic acid/methanol | 6 | 70.3 | 470 |
| 14 | 3% salicyclic acid/methanol | 5 | 71.5 | 468 |
| 15 | 3% acetic acid/tetrahydrofuran | 21 | 71.8 | 464 |
| 16 | 3% acetic acid/acetonitrile | 13 | 70.8 | 480 |
| 17 | 3% ethylenediamine/methanol | 12 | 63.2 | 470 |

The experiments illustrated in the above table show the advantageous effect of the washing procedure of the present invention upon the regeneration of used supported silver catalysts. It can be seen that the use of solubilizing agents in the washing compositions significantly decreases the number of washings necessary to reduce the potassium level to the desired amount and raise the selectivity of the catalyst in comparison to the number of washings necessary to achieve the same results when the solubilizing agents are not used. Thus, the method of the present invention is faster and more economical than prior processes. It is thought that the results of Example 17 using ethylenediamine and methanol were unsatisfactory because of the presence of the amine compound in the regeneration step since Example 7 without regeneration produced good results.

EXAMPLE 18

The experiments recorded below are comparative experiments which show the superiority of the process of the present invention over the process of U.S. Pat. No. 4,186,106 discussed above. In all three cases, the experiments were performed using the composition of the present invention and also with the composition specifically used in U.S. Pat. No. 4,186,106. The wash composition of the present invention, methanol containing 3 percent salicylic acid, was compared with pure methanol as used in Example 1 of the above patent. 60 milliliters of the wash compositions were poured at 25° C. over 60 grams of a commercial catalyst which had been used for the manufacture of ethylene oxide by direct oxidation of ethylene with oxygen. The mixture was left to stand for five hours in a 100 milliliter Erlenmeyer flask. The wash compositions were decanted and another 60 milliliters of the wash compositions were poured over the catalyst. After five hours, the wash compositions were again poured off. Next, a solution of 60 milliliters of methanol and 0.017 grams of cesium acetate were poured over the catalyst samples (which were still moist with methanol) in the 100 milliliter Erlenmeyer flask. The mixtures were left to stand for one hours, the impregnating solution poured off, and the catalyst samples dried for one hour at 110° C. in a drying cabinet. The catalyst samples were introduced into a test reactor and used to manufacture ethylene oxide at the same conditions as in the other examples. As can be seen by examining Table 3, the productivity of the catalyst sample treated with the composition of the present invention was significantly greater than the catalyst sample treated according to U.S. Pat. No. 4,186,106.

The procedure of Example 2 of the above patent was repeated using a composition comprising isopropanol and 3 percent salicylic acid according to the present invention and a washing liquid of isopropanol and 20 percent by weight of water as described in the above patent. The washing liquids were poured in three repetitions, over a 60 gram sample of the above catalyst in a 100 milliliter Erlenmeyer flask. After the last decantation, the washed catalyst samples were treated as described above with a solution of 0.017 grams of cesium acetate in 60 milliliters of methanol and then used to manufacture ethylene oxide in accordance with the above procedure. As can be seen in Table 3, the productivity of the catalyst sample treated with a composition of the present invention was almost twice as high as the catalyst sample treated according to U.S. Pat. No. 4,186,106.

A wash liquid consisting of acetone and 3 percent acetic acid according to the present invention and another sample consisting of acetone according to Example 4 of the above patent were poured at 25° C. over 60 grams of the catalyst used in the first experiment. The whole mixture was left to stand for one hour in a 200 milliliter Erlenmeyer flask. After decantation of the washing liquids, another 60 milliliters of washing liquid was poured over the catalyst samples and decanted after one hour. The samples were soaked in a flask in 60 milliliters of an methanolic solution containing 0.017 grams of cesium acetate and left to stand for one hour. After decantation of the excess amount of the impregnating solution, the catalyst portion was dried for one hour at 110° C. in a drying cabinet. The treated catalyst samples were put into the test reactor. As can be seen by looking at Table 3, the productivity of the catalyst treated with the composition of the present invention had a higher productivity than the composition treated according to U.S. Pat. No. 4,186,106.

In order to completely understand these comparative experiments, it must be pointed out that the conditions and procedures used in the above tests were those specified in U.S. Pat. No. 4,186,106. The composition of the present invention gave better performance even when used according to the procedures recommended by its competition. If the procedures and conditions specified in this application are used, the comparison between the composition of the present invention and the composition of U.S. Pat. No. 4,186,106 is even more weighted in favor of the composition of the present invention.

TABLE 3

| | EO Productivity | |
|---|---|---|
| Example | Present Invention | 4,186,106 |
| 1 | .20 | .14 |
| 2 | .90 | .47 |

TABLE 3-continued

| | EO Productivity | |
|---|---|---|
| Example | Present Invention | 4,186,106 |
| 4 | .34 | .31 |

I claim:

1. A method for removing alkali metal-containing impurities from supported silver catalysts which have been used for the direct oxidation of ethylene to ethylene oxide which comprises washing the catalyst with a composition which is comprised of in inert organic liquid and about 0.1% to about 10%, by weight, of solubilizing agent which is selected from the group consisting of aliphatic and aromatic acids.

2. The method of claim 1 wherein the inert organic liquid is selected from the group consisting of aliphatic, alicyclic, and aromatic hydrocarbons, ethers, alcohols, and ketones, and aliphatic and aromatic esters, amines, amides, aldehydes, and nitriles.

3. The method of claim 2 wherein the concentration of the solubilizing agent is from about 0.1% to about 5%.

4. The method of claim 3 wherein the washing procedure is carried out from 1 to 25 times.

5. The method of claim 1 wherein the solubilizing agent is selected from the group consisting of acetic acid, propionic acid, lactic acid, and salicylic acid.

6. A method of regenerating a supported silver catalyst which has been used for the direct oxidation of ethylene to ethylene oxide which comprises washing the catalyst to remove alkali metal-containing impurities with a composition comprised of an inert organic liquid and about 0.1% to about 10%, by weight, of a solubilizing agent which is selected from the group consisting of aliphatic and aromatic acids, and then applying to the catalyst from 1 to 1000 parts per 1 million parts of catalyst of cesium, rubidium, or a mixture thereof.

7. The method of claim 6 wherein the inert organic liquid is selected from the group consisting of aliphatic, alicyclic, and aromatic hydrocarbons, ethers, alcohols, and ketones, and aliphatic and aromatic esters, amides, aldehydes, and nitriles.

8. The method of claim 7 wherein the concentration of the solubilizing agent is from about 0.1% to about 5%.

9. The method of claim 8 wherein the washing procedure is carried out from 1 to 25 times.

10. The method of claim 6 wherein the solubilizing agent is selected from the group consisting of acetic acid, propionic acid, lactic acid, and salicylic acid.

11. In a method for regenerating a supported silver catalyst which has been used for the direct oxidation of ethylene to ethylene oxide which comprises washing the catalyst with an inert organic liquid and then applying to the catalyst from 1 to 1000 parts per 1 million parts of catalyst of cesium, rubidium, or a mixture thereof, the improvement which comprises removing alkali metal-containing impurities by including about 0.1% to about 10% by weight, of a solubilizing agent in the inert organic liquid, said solubilizing agent selected from the group consisting of aliphatic and aromatic acids.

12. The method of claim 11 wherein the inert organic liquid is selected from the group consisting of aliphatic, alicyclic, and aromatic hydrocarbons, ethers, alcohols, and ketones, and aliphatic and aromatic esters, amides, aldehydes, and nitriles.

13. The method of claim 12 wherein the concentration of the solubilizing agent is from about 0.1% to about 5%.

14. The method of claim 13 wherein the washing procedure is carried out from 1 to 25 times.

15. The method of claim 11 wherein the solubilizing agent is selected from the group consisting of acetic acid, propionic acid, lactic acid, and salicylic acid.

* * * * *